United States Patent [19]

Morrison, Jr. et al.

[11] Patent Number: 4,985,858
[45] Date of Patent: Jan. 15, 1991

[54] METHOD AND APPARATUS FOR TEMPERATURE DETERMINATION

[75] Inventors: Philip W. Morrison, Jr., South Windsor; Peter R. Solomon, West Hartford; David G. Hamblen, East Hampton, all of Conn.

[73] Assignee: Advanced Fuel Research, Inc., East Hartford, Conn.

[21] Appl. No.: 356,078

[22] Filed: May 23, 1989

[51] Int. Cl.⁵ .......................... G01J 5/08; G01N 21/62
[52] U.S. Cl. .................................... 364/557; 374/129; 356/43
[58] Field of Search ..................... 364/557; 250/338.1; 374/130, 134, 180, 129; 356/43

[56] References Cited

U.S. PATENT DOCUMENTS

| | | | |
|---|---|---|---|
| 4,506,158 | 3/1985 | Cadwallader et al. | 250/338.1 |
| 4,627,008 | 12/1986 | Rosenthal | 250/338.1 |
| 4,652,755 | 3/1987 | Solomon et al. | 250/341 |
| 4,708,493 | 11/1987 | Stein | 356/43 |
| 4,799,788 | 1/1984 | Berthet et al. | 356/45 |
| 4,840,496 | 6/1989 | Elleman et al. | 374/130 |
| 4,841,150 | 6/1989 | Walter | 356/43 |
| 4,845,647 | 7/1989 | Dils et al. | 364/557 |
| 4,924,478 | 5/1990 | Tank | 364/557 |

Primary Examiner—Thomas G. Black
Assistant Examiner—Michael Zanelli
Attorney, Agent, or Firm—Ira S. Dorman

[57] ABSTRACT

An optical technique for determining surface temperature utilizes the Christiansen effect that is exhibited by dielectric materials; i.e., strong absorption bands at certain wavenumber values, causing the radiance of the material to be that which would characterize a theoretical black body at that wavenumber value.

26 Claims, 2 Drawing Sheets

METHOD AND APPARATUS FOR TEMPERATURE DETERMINATION

The United States Government has rights in this invention pursuant to Contract No. DASG60-88-C-0083 awarded by the United States Department of Defense (Strategic Defense Initiative Office).

BACKGROUND OF THE INVENTION

There are many instances in which it is necessary or desirable to measure the temperature of a surface in situ, under conditions in which it is impractical or impossible to provide direct contact by a thermocouple or other form of mechanical probe. For example, it is not feasible to determine accurately the surface temperature of a deposit produced in a thin film-depositing reactor, either by contacting the film surface with a probe or by removing the deposit from the substrate.

Apparatus by which temperature measurements can be made remotely, and through optical means, are of course known in the art. One such instrument, for measuring the temperature of a target of unknown emissivity, is taught in Stein U.S. Pat. No. 4,708,493, issued Nov. 24, 1987. In accordance with it, first signals are derived from portions of radiation, from a thermally emitting target, occurring at two spaced wave lengths, and second signals are derived from reflected portions of two incident beams of radiation, at the same wave lengths. The derived signals are used to compute the temperature of the target.

Notwithstanding such prior art, a need exists for a relatively straight-forward and facile method by which the surface temperature of a sample can readily and accurately be determined in situ and without physical contact, and to provide apparatus for carrying out such a method; accordingly, it is the broad object of the invention to provide such a novel method and apparatus.

More specific objects of the invention are to provide such a method and apparatus which function through optical principles to determine the surface temperature of a target whose emissivity is unknown, and which afford means by which such emissivities can readily be determined.

SUMMARY OF THE INVENTION

It has now been found that certain of the foregoing and related objects of the invention are readily attained by the provision of a method in which spectral electromagnetic radiation (desirably in the region of of values of wavenumber between 10,000 and 200 $cm^{-1}$; i.e., the wave length region between 1 and 50 microns) is caused to impinge upon and reflect from the surface of a sample, to thereby identify any wavenumber value "v" of the incident radiation a which there is substantially zero reflectance, the sample being of sufficient thickness to prevent substantially transmittance of electromagnetic radiation of wavenumber value v through it. Radiance from the surface, at wavenumber value v, is measured and is correlated to the radiance of a theoretical black body at the same wavenumber value v to determine the surface temperature T. The steps of identifying wavenumber value v and of measuring radiance will usually be carried out concurrently, although the zero reflectance point(s) may be predetermined.

In some embodiments of the method, a curve representative of spectral radiance from the surface will be generated in the radiance-measuring step, and the correlating step will be effected by identifing the black body curve having the same value of radiance as the measured value, at wavenumber value v; this may be done either by selecting the Planck (black body) curve having a matching amplitude at the point v or (when at least two zero reflectance wavenumber values have been identified) by a curve fitting routine. Alternatively, the correlating step can be effected by application of the general equation:

$$R = C_1 v^3 / exp\{C_2 v / T\} - 1$$

in which R represents the measured radiance, expressed in watts/steradian $cm^2$ $cm^{-1}$; in which the quantity to which R is equal is the wavenumber-dependent Planck function for a theoretical black body at temperature T, expressed in Kelvins and at wavenumber v, and in which $C_1$ and $C_2$ are constants having the values $1.191 \times 10^{-12}$ watts/steradian $cm^2$ $(cm^{-1})^4$ and 1.439 K cm, respectively. Generally, the radiance measurement will be carried out using an optical instrument having an instrument response function W, with R in the foregoing equation being equal to S/W, S being the measured value (e.g., voltage) representative of radiance at wavenumber value v. It will be understood that as used herein the designations "R", "S" and "W" are spectral values. For certain applications, the instrument employed will most advantageously be a Fourier-transform infrared spectrometer, which will also be utilized to carry out the correlating step of the method. The method may include the additional step of dividing the measured spectral radiance by the spectral radiance of a theoretical black body at the thus-determined temperature T, to determine the spectral emissivity of the sample.

Other objects of the invention are attained by the provision of apparatus comprising: means for causing spectral electromagnetic radiation to impinge upon a sample, so as to produce reflection of electromagnetic radiation from the surface thereof; means for detecting electromagnetic radiation reflected from the sample surface, and for identifying any wavenumber value "v" of the incident radiation at which there is substantially zero reflectance; means for measuring spectral radiance from the surface, including radiance at wavenumber value v; and means for correlating the measured radiance to the radiance of a theoretical black body at wavenumber value v to determine the surface temperature "T" of the sample.

The correlation means will, in some embodiments, be adapted to identify the black body curve having the same value of radiance, at wavenumber value v, as the measured value. The apparatus will usually additionally include electronic data processing means for identifying the zero reflectance point(s) and for so correlating the measured radiance, and in certain embodiments the data processing means will be programmed to correlate the measured radiance by application of the general equation: $R = C_1 v^3 / exp\{C_2 v / T\} - 1$ the terms of which have hereinabove been defined.

The apparatus will preferably additionally include means for enabling the "detecting" means and the "measuring" means to perform their functions concurrently, and the means for measuring will usually comprise an optical instrument having an instrument response function W, the data processing means being programmed to apply that function, as previously described; for certain applications the apparatus will preferably comprise a Fourier-transform infrared spectrometer. Finally, the data processing means of the apparatus may be programmed to divide the spectral radiance of the sample by the spectral radiance of a theoretical black body at temperature T, so as to thereby determine the spectral emissivity of the sample.

DETAILED DESCRIPTION OF THE ILLUSTRATED EMBODIMENT

Figure 1:
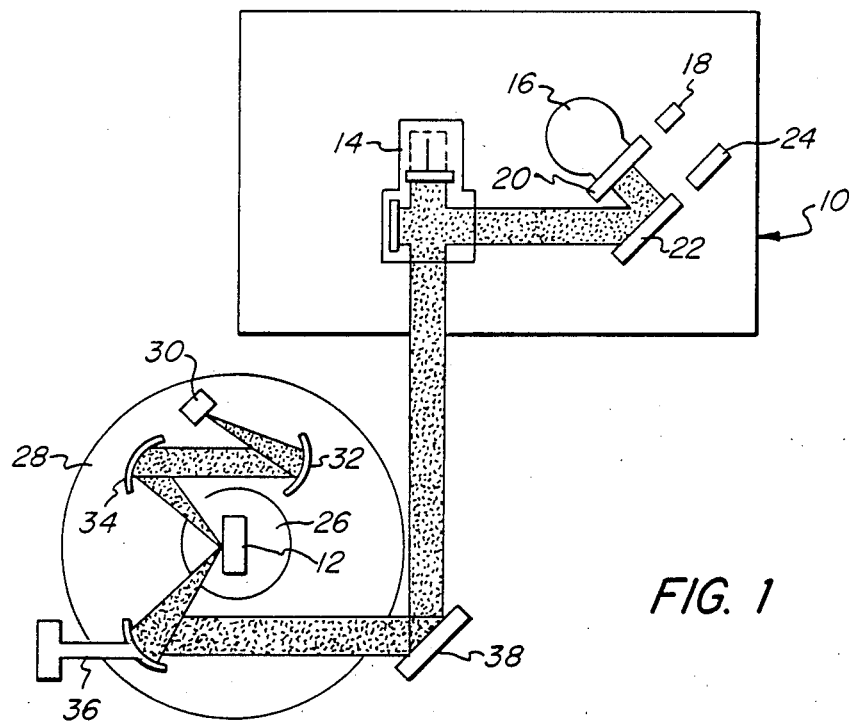
FIG. 1 is a schematic representation of apparatus embodying the present invention.

Turning to FIG. 1 of the appended drawings, therein schematically illustrated is apparatus embodying the invention and comprised of a Fourier-transform infrared spectrometer (FT-IR), generally designated by the numeral 10, augmented with means for establishing appropriate optical paths to and from the sample 12. The FT-IR 10 includes an interferometer 14, an infrared radiation source 16, an emission detector 18, a movable mirror 20, and two fixed mirrors 22 and 24. The sample 12 is situated upon a stage 26, about which is rotatably disposed an annular platform 28, the latter carrying a radiation detector 30 and two mirrors 32 and 34. Mounted externally of the platform and stage are two additional mirrors, 36 and 38.

In the optical path configuration shown in FIG. 1, established by the mirrors 32, 34, 36 and 38 and as indicated by the shaded beam, the apparatus is arranged to measure that portion of the spectral radiation, emanating from the FT-IR, which is reflected from the surface of the sample 12 to the detector 30. In the mode of operation illustrated, the movable mirror 20 of the FT-IR is operatively displaced so as to permit the beam to be projected from source 16 onto the mirror 22.

As an alternative configuration (not shown) for measuring emission from the sample 12, the movable mirror 20 is operatively positioned in front of the source 16, so as to block radiation therefrom. The radiation emitted from the sample 12 travels sequentially along a path to the mirrors 36 and 38 and through the interferometer 14, then to be reflected by the mirrors 22, 20 and 24 to the emission detector 18. It will be appreciated by those skilled in the art that the reflectance and emission measurements will normally be made concurrently, by suitable manipulation of the mirror 20; a half-mirrored, half-transparent plate, or other form of diverter, may be substituted at that location if so desired. It will also be appreciated that the positioning of the sample 12 may be varied from that shown, to achieve an optimal orientation for making the necessary measurements.

The arrangement shown in FIG. 1 can also be utilized to make radiation transmittance measurements. To do so the platform 28 need only be rotated to operatively position the detector 30 behind the sample 12. This will generally be unnecessary, however, because the sample employed will normally be of sufficient thickness to permit it to be assumed that the necessary opacity exists.

Figure 2:
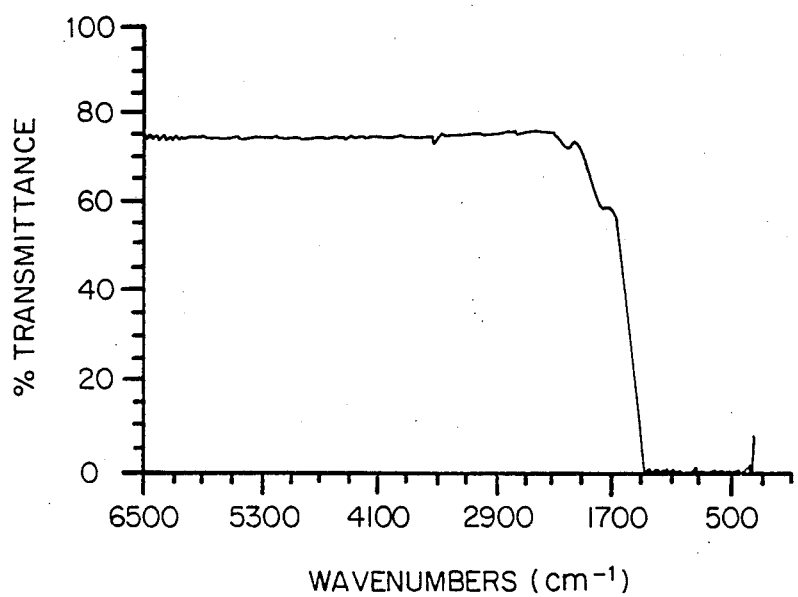
FIGS. 2, 3 and 4 are graphical representations of measurements made in accordance with the method of the invention.
Figure 3:
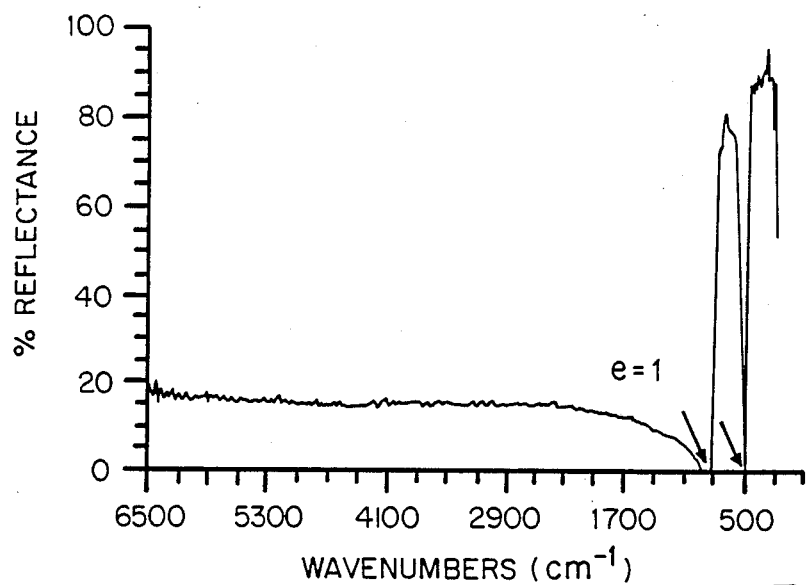
Figure 4:
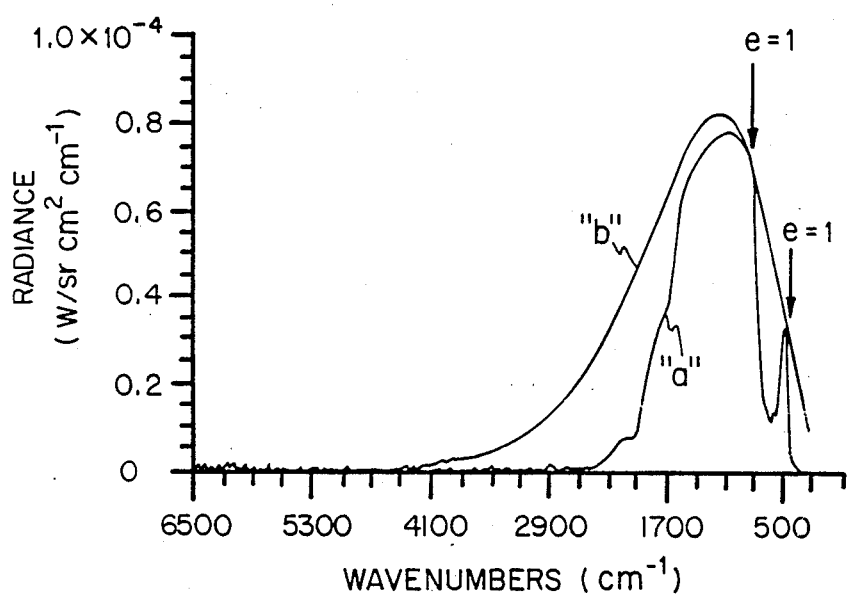

Exemplary of the efficacy of the present invention is the following specific example, taken with further reference to FIG. 1 and with reference to FIGS. 2-4.

EXAMPLE ONE

Utilizing as the sample 12 a slab of strontium titanate one millimeter in thickness and heated (by means not shown) to an unknown temperature, transmission measurements are made by causing electromagnetic radiation, in the spectral range of about 6500 to 300 cm$^{-1}$, to impinge upon the sample; a Bomem Michelson 102 FT-IR spectrometer is employed. As is graphically shown in FIG. 2, it is thereby determined that the slab is opaque to radiation at wavenumber values below 1400 cm$^{-1}$; therefore, incident radiation within that spectral region must either be reflected o absorbed by the sample.

Reflectance measurements are made over the same spectral range, from which it is determined (as graphically shown by FIG. 3) that the sample exhibits zero (or negligible) reflectance at two wavenumber values, i.e., 870 cm$^{-1}$ and 482 cm$^{-1}$; it is well known that this phenomenon, referred to as the "Christiansen effect," occurs in most dielectric materials. Curve "a" of FIG. 4 shows the emission spectrum of the sample 12, as indicated by voltage readings from the detector 18.

Utilizing these data and measurements the temperature of the sample 12 is determined, by both of two methods, to have a value of 542° Kelvin. The first method is represented in FIG. 4, and involves a curve-fitting routine carried out by use of the computer of the FT-IR, suitably programmed for the purpose.

Because, as noted hereinabove, strontium titanate has a negligible or zero reflectance value at 870 and 482 cm$^{-1}$, the sample is known to be completely absorbing; i.e., that it acts like a theoretical black body at those wavenumbers. By identifying the theoretical black body curve that coincides with the measured curve (a) at 870 and/or 482 cm$^{-1}$, the temperature "T" of the sample is determined. Coinciding curve (b) of FIG. 4 represents the spectral radiance of a theoretical black body at the temperature 542° K; thus, T is determined to have the same value.

As an alternative to utilizing the curve-fitting routine described above, the temperature can be calculated. Again the knowledge that a sample exhibits black body radiation characteristics, at at least one wavenumber, is utilized.

The reading "S" from the emission detector 18 corresponding to 870 cm$^{-1}$ is 1.43 volts (the higher of the two Christiansen point values is used because of the more favorable signal:noise ratio afforded). Dividing that value by the instrument response function "W" of the FT-IR (the value of W being $1.92 \times 10^4$ volts/watts/steradian cm$^2$ cm$^{-1}$) provides an radiance of $7.44 \times 10^{-5}$ watts/steradian cm$^2$ cm$^{-1}$. Setting that quantity in turn equal to $C_1 v^3 / \exp\{C_2 v/T\} - 1$ and substituting the values $1.191 \times 10^{-12}$ watts/steradian cm$^2$ (cm$^{-1}$)$^4$, 1.439 K cm, and 870, for $C_1$, $C_2$ and $v$, respectively, enables the temperature T to be calculated; it is found to have a value of 542° K.

The temperature of a sample, as an element of the Planck function "H", is related to its spectral emission R by the generalized expression:

$$R = e(v) \times H(v, T)$$

in which "e(v)" represents the spectral emissivity of the sample (at wavenumber value v). Where, as is prerequisite to the instant technique the sample surface exhibits substantially zero reflectivity at some wavelength of incident radiation, it is (as an effective black body) known to be completely absorbing, and hence to have an emissivity of unity. Consequently, the foregoing expression relating S/W directly to the Planck function (with no emissivity factor) applies.

The instrument response function is derived from calibration measurements in which the apparatus is conditioned to measure black body emissions at two temperatures, as may conveniently be done by creating a black body cavity at the location (such as the stage 26) at which the sample would otherwise be situated. Correcting the detector voltage reading with the instrument response function eliminates the effects of incidental and background radiation, beam path optics, and the like, to thereby provide an accurate (i.e., true physical) representation of the sample emission.

The technique of the invention is applicable to measure temperatures of dielectric materials that exhibit strong radiation absorption bands, producing zero or negligible reflectance at one or more wavelengths. It may also be used with conducting samples having a dielectric surface layer (produced for example by coating, by oxidation of a metallic substrate, etc.); as far as is known conducting materials do not exhibit the Christiansen effect, but to the extent that they may do so the present invention is equally applicable thereto. As noted above, the sample must also be opaque to radiation at the Christiansen point wavelength used for the emission measurement, and that condition will normally be inherent in the thickness of the sample employed. Although use of radiation in the infrared range will generally be preferred in the practice of the instant method, other regions, such as the visible and low ultraviolet, may be employed as long as adequate black body intensity, and Christiansen points, are available therewithin.

While the invention is not limited to any particular embodiment of apparatus, it will be appreciated that an FT-IR spectrometer-based system offers a number of very significant benefits, particularly for general scientific applications of the method. FT-IR spectroscopy permits rapid collection of complete spectra, its interferometer inherently permits amplitude modulation of radiation from the source and from the sample, compact and rugged FT-IR instruments are commercially available, and its integrated computer is available for automation of the method, for sample reduction, and for manipulation of the measured values and data. Notwithstanding the foregoing, it will be appreciated that other systems may be preferred for some applications, such as to afford a higher degree of portability for on-site process monitoring. For example, apparatus utilizing systems of selective filters, to produce radiation of desired wavelengths, may be employed to good advantage under appropriate circumstances.

Thus, it can be seen that the present invention provides a relatively straight-forward and facile method by which the surface temperature of a sample can readily and accurately be determined, in situ and without physical contact, and that it provides novel apparatus by which the method can readily be carried out. The method and apparatus function through optical principles to determine the surface temperature of a sample whose spectral emissivity is unknown, and they provide means by which such emissivities can readily be determined.

Having thus described the invention, what is CLAIMED is:

1. In a method for the determination of the surface temperature of a sample by optical means, the steps comprising:
   a. causing spectral electromagnetic radiation to impinge upon a sample so a to produce reflection of electromagnetic radiation from the surface thereof, and thereby identifying any wavenumber value "v" of the incident radiation at which there is substantially zero reflectance from said surface, said sample being of a thickness sufficient to prevent substantially transmittance of electromagnetic radiation of wavenumber value v therethrough;
   b. measuring spectral radiance from said surface at wavenumber value v; and
   c. correlating said measured radiance to the radiance of a theoretical black body at wavenumber value v to determine said temperature "T".

2. The method of claim 1 wherein said steps a and b are carried out concurrently.

3. The method of claim 1 wherein a curve representative of spectral radiance from said surface is generated in said step b, and wherein said correlating step c is effected by identifying the black body curve having the same value of radiance as said measured value at said wavenumber value v.

4. The method of claim 1 wherein said radiation caused to impinge upon said sample includes the spectral region of 10,000 $cm^{-1}$ to 200 $cm^{-1}$.

5. The method of claim 4 wherein said method includes the additional step of dividing said measured spectral radiance by the spectral radiance of a theoretical black body at said temperature T, to determine the spectral emissivity of said sample.

6. The method of claim 1 wherein the sample comprises a substrate and a surface layer, said layer being of a dielectric composition and being different from the composition of said substrate.

7. The method of claim 6 including the additional steps of preparing and providing a sample, said step of preparing entailing the formation of said layer on said substrate.

8. The method of claim 1 wherein said correlating step c is effected by application of the general equation:

$$R = C_1 v^3 / exp\{C_2 v/T\} - 1$$

in which R represents said measured radiance, expressed in watts/steradian $cm^2$ $cm^{-1}$; in which the quantity to which R is equal is the wavenumber-dependent Planck function for a theoretical black body at temperature T, expressed in degrees Kelvin and at wavenumber value v, and in which $C_1$ and $C_2$ are constants having the values $1.191 \times 10^{-12}$ watts/steradian $cm^2$ $(cm^{-1})^4$, and 1.439 K cm, respectively.

9. The method of claim 8 wherein said step b is carried out using an optical instrument having an instrument response function W, and wherein R is equal to S/W and S is the measured value representative of radiance at said wavenumber value v, W and S being spectral values.

10. The method of claim 9 wherein said instrument comprises a Fourier-transform infrared spectrometer, and wherein said correlating step c is also carried out therewith.

11. In a method for the determination of the surface temperature of a sample by optical means, the steps comprising:

a. identifying any wavenumber value "v" of radiation at which there is substantially zero reflectance from the surface of a sample;
b. measuring spectral radiance from said surface at wavenumber value v; and
c. correlating said measured radiance to the radiance of a theoretical black body at wavenumber value v to determine said temperature "T".

12. The method of claim 11 wherein a curve representative of spectral radiance from said surface is generated in said step b, and wherein said correlating step c is effected by identifying the black body curve having the same value of radiance as said measured value at said wavenumber value v.

13. The method of claim 11 wherein said correlating step c is effected by application of the general equation:

$$R = C_1 v^3 / exp\{C_2 v / T\} - 1$$

in which R represents said measured radiance, expressed in watts/steradian cm$^2$ cm$^{-1}$; in which the quantity to which R is equal is the wavenumber-dependent Planck function for a theoretical black body at temperature T, expressed in degrees Kelvin and at wavenumber value v, and in which $C_1$ and $C_2$ are constants having the values $1.191 \times 10^{-12}$ watts/steradian cm$^2$ (cm$^{-1}$)$^4$, and 1.439 K cm, respectively.

14. The method of claim 13 wherein said step b is carried out using an optical instrument having an instrument response function W, and wherein R is equal to S/W and S is the measured value representative of radiance at said wavenumber value v, W and S being spectral values.

15. The method of claim 11 wherein the sample comprises a substrate and a surface layer, said layer being of a dielectric composition and being different from the composition of said substrate.

16. The method of claim 15 including the additional steps of preparing and providing a sample, said step of preparing entailing the formation of said layer on said substrate.

17. Apparatus adapted for use in optically determining the surface temperature of a sample, comprising:
a. means for causing spectral electromagnetic radiation to impinge upon a sample so as to produce reflection of electromagnetic radiation from the surface thereof;
b. means for detecting electromagnetic radiation reflected from the surface of such a sample, and for identifying any wavenumber value "v" of the incident radiation at which there is substantially zero reflectance from the surface;
c. means for measuring spectral radiance from the surface, including radiance at wavenumber value v; and
d. means for correlating the measured radiance to the radiance of a theoretical black body at wavenumber value v to determine the temperature "T".

18. The apparatus of claim 17 wherein said means for correlating identifies the black body curve the same value of radiance as the value measured by said means for measuring, both at said wavenumber value v.

19. The apparatus of claim 17 additionally including means for enabling said means for detecting and said means for measuring to perform their functions concurrently.

20. The apparatus of claim 17 wherein said means for causing radiation to impinge produces an electromagnetic spectrum including the spectral region of 10,000 cm$^{-1}$ to 200 cm$^{-1}$.

21. The apparatus of claim 17 additionally including electronic data processing means for so identifying substantially zero reflectance, and for so correlating the measured radiance.

22. The apparatus of claim 21 wherein said data processing means divides the measured spectral radiance from the surface of the sample by the spectral radiance of a theoretical black body at the determined temperature T, so as to determine the spectral emissivity of the sample.

23. The apparatus of claim 21 wherein said data processing means is programmed to so correlate the measured radiance by application of the general equation:

$$R = C_1 v^3 / exp\{C_2 v / T\} - 1$$

in which R represents the radiance measured by said means for measuring, at wavenumber value v and expressed in watts/steradian cm$^2$ cm$^{-1}$; in which the quantity to which R is equal is the wavenumber-dependent planck function for a theoretical black body at temperature T, expressed in degrees Kelvin and at wavenumber value v; and in which $C_1$ and $C_2$ are constants having the values $1.191 \times 10^{-12}$ watts/steradian cm$^2$ (cm$^{-1}$)$^4$, and 1.439 K cm, respectively.

24. The apparatus of claim 23 wherein said means for measuring comprises an optical instrument having an instrument response function W, and wherein said data processing means is programmed to apply said function W in effecting such measured radiance correlation by setting R equal to S/W, where S is the value representative of radiance at wavenumber value v measured by said means for measuring, W and S being spectral values.

25. The apparatus of claim 24 comprising a Fourier-transform infrared spectrometer.

26. Apparatus adapted for use in optically determining the surface temperature of a sample, comprising: a Fourier-transform infrared spectrometer providing means for producing a beam of spectral electromagnetic radiation; means for operatively positioning a sample for impingement by the beam from said radiation-producing means, so as to produce reflection of electromagnetic radiation from the surface thereof; and means for detecting electromagnetic radiation reflected from the surface of such a sample, said spectrometer having means for identifying any wavenumber value "v" of the radiation beam impinging upon the sample at which there is substantially zero reflectance from the surface thereof, means for measuring spectral radiance from the surface, including radiance at wavenumber value v, and means for correlating the measured radiance to the radiance of a theoretical black body at wavenumber value v, to determine the temperature "T".

* * * * *

UNITED STATES PATENT AND TRADEMARK OFFICE
CERTIFICATE OF CORRECTION

PATENT NO. : 4,985,858

DATED : January 15, 1991

INVENTOR(S) : Morrison, Jr. et al

It is certified that error appears in the above-identified patent and that said Letters Patent is hereby corrected as shown below:

On the title page, under "References Cited, the following should appear:

OTHER PUBLICATIONS

"Normal emittance measurements by a transient temperature technique" (Robert J. Tiernan & James E. Saunders), J. Appl. Phys. 64(2), 15 July, 1988

"Analysis of particle emittance, composition, size and temperature by FT-i.r. emission/transmission spectroscopy" (Solomon et al) FUEL, Vol. 66, July, 1987

Column 6, line 5, change "a" (second instance) to --as--

Column 7, line 61, insert after the word "curve" --having--

Column 8, line 29, the name "planck" should be capitalized.

Column 4, line 13, change "o" to --or--

Signed and Sealed this

Ninth Day of June, 1992

*Attest:*

DOUGLAS B. COMER

*Attesting Officer*   Acting Commissioner of Patents and Trademarks